United States Patent
Metten et al.

(10) Patent No.: US 9,095,526 B2
(45) Date of Patent: *Aug. 4, 2015

(54) AGENT FOR TEMPORARILY DEFORMING KERATIN FIBERS BASED ON A COMBINATION OF SPECIFIC FILM-FORMING POLYMERS

(71) Applicant: Henkel AG & Co. KGaA, Dusseldorf (DE)

(72) Inventors: Diane Metten, Hamburg (DE); Bernd Richters, Hamburg (DE); Rene Scheffler, Ellerau (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,791

(22) PCT Filed: Dec. 11, 2012

(86) PCT No.: PCT/EP2012/075010
§ 371 (c)(1),
(2) Date: Jun. 20, 2014

(87) PCT Pub. No.: WO2013/092285
PCT Pub. Date: Jun. 27, 2013

(65) Prior Publication Data
US 2015/0017112 A1     Jan. 15, 2015

(30) Foreign Application Priority Data
Dec. 20, 2011 (DE) .......................... 10 2011 089 172

(51) Int. Cl.
*A61Q 5/06* (2006.01)
*A61K 8/73* (2006.01)
*A61K 8/81* (2006.01)

(52) U.S. Cl.
CPC ............... *A61K 8/731* (2013.01); *A61K 8/8147* (2013.01); *A61K 8/8152* (2013.01); *A61Q 5/06* (2013.01)

(58) Field of Classification Search
CPC ....... A61Q 5/06; A61K 8/731; A61K 8/8152; A61K 8/147; A61K 2800/594
USPC .................................. 424/70.13, 70.16, 70.28
See application file for complete search history.

(56) References Cited

U.S. PATENT DOCUMENTS

2003/0223948 A1* 12/2003 Maubru .................... 424/70.13
2009/0068136 A1*  3/2009 Beumer et al. ............ 424/70.16

FOREIGN PATENT DOCUMENTS

EP        1348420 A1     10/2003

OTHER PUBLICATIONS

ISA EPO, International Search Report and Written Opinion for International Application No. PCT/EP2012/075010, dated Sep. 1, 2014.
Database GNPD [Online]. MINTEL; Apr. 1, 2011. Redken: "Full Frame 07 Mousse," XP002728636. Database accession No. 1517864, product description ingredients.
Database GNPD [Online]. MINTEL; May 1, 2008. L'Oreal: "Amped Up Mega Mousse," XP002728637. Database accession No. 905663, product description ingredients.
Database GNPD [Online]. MINTEL; Sep. 1, 2010. Matrix Essentials: "Firmfix Gel," XP002728638. Database accession No. 1384441, product description ingredients.
Lubrizol: "Hair Styling Cream with Natural Oils & Conditioners," Nov. 30, 2010. pp. 1-2. XP055135296. Retrieved from the Internet: URL:http://www.lubrizol.comjPersonalCare/S-X0007-Hair-Styling-Cream-with-Natural-Oils-Conditioners.pdf, [retrieved on Aug. 19, 2014].
"CELQUAT L-200 (Polyquaternium-4)". Sep. 15, 2008. pp. 1-21. XP055135400. Retrieved from the Internet:URL:http://www.ptdju.comjresourcesjexternal/65D3886E-4434-4D8A-9088-CFE2C29E4C7F/Personal Care/Skin CareApplication/ConditioningAgent/BrochurejCelquat L-200 documentbundle.pdf. [retrieved on Aug. 19, 2014].

* cited by examiner

*Primary Examiner* — Eisa Elhilo
(74) *Attorney, Agent, or Firm* — P. Scott Smith

(57) ABSTRACT

A cosmetic agent, containing in a cosmetically acceptable carrier: a) at least one copolymer A of allyl methacrylate with one or more monomers selected from acrylic acid, methacrylic acid, acrylic acid esters and methacrylic acid esters, b) at least one polymeric quaternary ammonium compound from the group of quaternized celluloses, is particularly suitable for temporarily deforming keratinic fibers.

9 Claims, No Drawings

AGENT FOR TEMPORARILY DEFORMING KERATIN FIBERS BASED ON A COMBINATION OF SPECIFIC FILM-FORMING POLYMERS

CROSS REFERENCE TO RELATED APPLICATIONS

The present disclosure is a U.S. National Stage entry under 35 U.S.C. §371 based on International Application No. PCT/EP2012/075010, filed Dec. 11, 2012 which was published under PCT Article 21(2) and which claims priority to German Patent Application No. 10 2011 089 172.2 filed on Dec. 20, 2011, which is incorporated herein by reference in its entirety.

TECHNICAL FIELD

The technical field describes cosmetic agents based on a specific polymer combination, use of these cosmetic agents for temporarily deforming keratinic fibers and cosmetic methods using these agents.

BACKGROUND

Polymers are widely used in the most varied cosmetic agents. They are to be found in agents for treating skin as well as in agents for treating hair, in agents which are washed off or out again directly after use, i.e. "rinse-off products", and in agents which remain on the skin or hair, i.e. "leave-on agents". The polymers are used for the most varied reasons and specific properties of the polymers are exploited in each case. In agents for treating skin, in shampoos, hair rinses and hair masks, the emphasis often lies on the thickening or conditioning properties of the polymers. In agents for temporarily deforming keratinic fibers, hereinafter also known as styling agents, alongside these properties film-forming and/or setting effects are particularly desired. Polymers often also serve as auxiliaries for improving or indeed enabling deposition and fixing of other active substances and ingredients on the skin or hair. By adding suitable polymers to hair coloring agents, for example, rubbing fastness and coloring durability may be increased.

Cosmetic agents generally contain individual polymers which are specifically tailored to achieving a very specific effect. If various effects are to be achieved, a plurality of polymers must be added. However, using too many different polymers may be associated with a series of disadvantages. Problems may accordingly arise during formulation, for instance because the polymers react with one another or with other components of the agent resulting in precipitation or decomposition phenomena. Certain polymers also have a tendency to be deposited so permanently on the skin and in particular on the hair that they are no longer completely removed with normal washing and the polymer accumulates undesirably so ultimately leading to contamination of the skin or hair.

There is therefore a constant need for polymers or suitable combinations of small numbers of polymers which simultaneously exhibit as many as possible of the desired properties.

For example, in the case of styling agents, the polymers used need to give the treated hair the strongest possible hold. In addition to a high degree of hold, styling agents must meet a whole series of further requirements. These may be broadly divided into properties on the hair, properties of the respective formulation, for example properties of the foam, the gel or the sprayed aerosol, and properties which affect the handling of the styling agent, wherein properties on the hair are of particular importance. Particular mention should be made of moisture resistance, low tackiness and a well-balanced conditioning effect. Moreover, a styling agent should as far as possible be universally applicable for all hair types. If the styling agent is a gel or a paste, the polymers should additionally have thickening properties.

SUMMARY

The object of the present disclosure was accordingly to provide further suitable polymer combinations which are distinguished by good film-forming and/or setting properties, have a very high level of hold without having to sacrifice flexibility and good moisture resistance, in particular perspiration and water resistance, and are additionally suitable for producing stably viscous and stably transparent cosmetic compositions.

These objects were achieved by a specific polymer combination. The present disclosure accordingly firstly provides a cosmetic agent, containing in a cosmetically acceptable carrier a) at least one copolymer A of allyl methacrylate with one or more monomers selected from acrylic acid, methacrylic acid, acrylic acid esters and methacrylic acid esters;
b) at least one polymeric quaternary ammonium compound from the group of quaternized celluloses.

The agents according to the disclosure contain the active substances in a cosmetic carrier. For the purposes of the disclosure, said cosmetic carrier is aqueous, alcoholic or aqueous-alcoholic. For the purposes of the present disclosure, aqueous-alcoholic carriers should be taken to be hydrous compositions containing about 3 to about 70 wt. % of a $C_1$-$C_4$ alcohol, in particular ethanol or isopropanol, relative to the total weight of the mixture for use. For the purposes of the disclosure, an aqueous carrier contains at least about 30 wt. %, in particular at least 50 wt. % water, relative to the total weight of the mixture for use. Preferred cosmetic agents contain, relative to the total weight thereof, about 40 to about 99 wt. %, for example about 50 to about 98 wt. %, such as about 60 to about 95 wt. % and in particular about 70 to about 90 wt. % water. The pH value (about 10% solution, about 20° C.) of preferred cosmetic agents amounts to about 4 to about 9, for example about 5 to about 8 and in particular about 6 to about 7.

The agents according to the disclosure contain as first essential component a copolymer A of allyl methacrylate with one or more monomers selected from acrylic acid, methacrylic acid, acrylic acid esters and methacrylic acid esters. The stated acrylic acid esters and methacrylic acid esters for example comprise $C_1$-$C_{12}$ alkyl acrylates and $C_1$-$C_{12}$ alkyl methacrylates, such as methyl acrylate, ethyl acrylate, propyl acrylate, methyl methacrylate, ethyl methacrylate, propyl methacrylate and mixtures thereof. It is more preferred to use a copolymer A of allyl methacrylate with one or more monomers a1) selected from acrylic acid and methacrylic acid; and one or more monomers a2) selected from acrylic acid esters and methacrylic acid esters.

For the technical effect of the agents according to the disclosure, it has proven advantageous for copolymer A to be based in a proportion of at least about 70 wt. %, for example of at least about 80 wt. %, for example of at least about 90 wt. % and in particular of at least about 95 wt. % on allyl methacrylate and one or more monomers from the group acrylic acid, methacrylic acid, acrylic acid esters and methacrylic acid esters.

It is technically more preferred for copolymer A to be based in a proportion of at least about 70 wt. %, for example of at least about 80 wt. %, for example of at least about 90 wt. % and in particular of at least about 95 wt. % on allyl methacrylate and one or more monomers from the group acrylic acid, methacrylic acid and one or more monomers from the group acrylic acid esters and methacrylic acid esters.

An exemplary copolymer A consists of the aminomethylpropanol salt of copolymers of allyl methacrylate with one or more monomers selected from acrylic acid, methacrylic acid, acrylic acid esters and methacrylic acid esters. A corresponding copolymer with the INCI name AMP-Acrylates/Allyl Methacrylate Copolymer is distributed by Noveon under the name Fixate™ G-100.

The proportion by weight of copolymer A in the total weight of cosmetic agents according to the disclosure for example amounts to about 0.05 to about 10 wt. %, for example about 0.1 to about 7.0 wt. % and in particular about 0.2 to about 5.0 wt. %.

The agents according to the disclosure contain as second essential component a polymeric quaternary ammonium compound from the group of quaternized celluloses.

Suitable quaternized celluloses may differ with regard to their degree of substitution, their cationic charge density, their nitrogen content and their molecular weight. Examples of quaternized celluloses are Polyquaternium-10, commercially offered for sale for example under the names Celquat® SC-230, Celquat® SC-240 (National Starch) and Polymer JR® 400 (Amerchol);

Polyquaternium-24, commercially offered for sale for example under the name Polymer Quatrisoft® LM-200 (Amerchol);

Polyquaternium-67, commercially offered for sale for example under the names Polymer® SL or Polymer® SK (Amerchol);

Polyquaternium-72, commercially offered for sale under the name Mirustyle® CP (Croda).

Preferred quaternized celluloses are obtained by "grafting". Preferred hydroxyalkylcelluloses, for example hydroxymethyl-, hydroxyethyl- and hydroxypropylcellulose, are in particular those which are grafted with a methacryloylethyltrimethylammonium salt, methacrylamidopropyltrimethylammonium salt or diallyldimethylammonium salt. Commercial products which meet this definition are in particular the products named Celquat® L 200 (INCI name: Polyquaternium-4) and Celquat® H 100 (INCI name: Polyquaternium-4) from National Starch.

In principle, all quaternized celluloses, but in particular the above-stated quaternized celluloses, are suitable for use in the cosmetic agents according to the disclosure. With regard to the cosmetic properties of these agents, however, the quaternized celluloses designated under the INCI name Polyquaternium-4, have proved to be particularly advantageous.

Cosmetic agents in which copolymer B is selected from the group of graft copolymers of hydroxyethylcellulose with diallyldimethylammonium chloride are therefore more preferred. In particular, those copolymers B which are based in a proportion of at least about 70 wt. %, for example of at least about 80 wt. %, for example of at least about 90 wt. % and in particular of at least about 95 wt. % on hydroxyethylcellulose and diallyldimethylammonium chloride are more preferred.

The proportion by weight of the polymeric quaternary ammonium compound from the group of quaternized celluloses in the total weight of cosmetic agents according to the disclosure for example amounts to about 0.05 to about 10 wt. %, for example to about 0.1 to about 7.0 wt. % and in particular to about 0.2 to about 5.0 wt. %.

The agents according to the disclosure are distinguished from cosmetic agents with alternative polymeric quaternary ammonium compounds not only by the above-stated advantages but in particular also by an improved level of hold. For the cosmetic properties of the agents according to the disclosure, a weight ratio of polymers A and B in the cosmetic agent of between about 8:1 and about 1:8, for example between about 6:1 and about 1:6 and in particular between about 4:1 and about 1:4 has proven particularly advantageous.

Copolymer A is used in the cosmetic agents for example in partially neutralized or neutralized form. At least one alkanolamine is for example used for neutralization. The alkanolamines usable as an alkalizing agent according to the disclosure are for example selected from primary amines with a $C_2$-$C_6$ alkyl parent substance which bears at least one hydroxyl group. Particularly preferred alkanolamines are selected from the group formed by 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Particularly preferred alkanolamines according to the disclosure are selected from the group 2-aminoethan-1-ol, 2-amino-2-methylpropan-1-ol and 2-amino-2-methylpropane-1,3-diol. 2-Amino-2-methylpropanol has proven to be a particularly suitable neutralizing agent. Cosmetic agents which are preferred according to the disclosure contain at least one alkanolamine, for example 2-amino-2-methylpropanol. 2-Amino-2-methylpropanol is used in the agents according to the disclosure for example in a quantity which does not exceed the quantity needed to neutralize copolymer A. The quantities of 2-amino-2-methylpropanol used in the agents according to the disclosure for example amount to about 80 to about 100%, such as about 90 to about 100% and in particular about 95 to about 100% of the quantity required for complete neutralization of copolymer A. In a preferred embodiment, the proportion by weight of 2-amino-2-methylpropanol in the total weight of the cosmetic agent amounts to about 0.1 to about 4.0 wt. %, for example about 0.2 to about 3.0 wt. % and in particular about 0.5 to about 2.0 wt. %.

In addition to the previously described copolymers and carrier substances, the cosmetic agents according to the disclosure may contain further ingredients. The group of these further ingredients in particular includes cosmetically active auxiliary substances and additives.

The cosmetic agents according to the disclosure contain as preferred component at least one quaternary ammonium compound. Monomeric or polymeric active substances may be used as the quaternary ammonium compound.

From the plurality of possible monomeric quaternary ammonium compounds, the compounds from the groups:

trimethylalkylammonium halides;

esterquats quaternary imidazolines have proven particularly effective.

The group of trimethylalkylammonium halides in particular includes the compounds of formula (Tkat1).

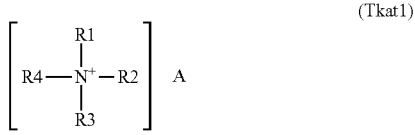
(Tkat1)

In the formula (Tkat1), R1, R2, R3 and R4 in each case mutually independently denote hydrogen, a methyl group, a phenyl group, a benzyl group, a saturated, branched or unbranched alkyl residue with a chain length of 8 to 30 carbon atoms, which may optionally be substituted with one or more hydroxyl groups. A denotes a physiologically acceptable anion, for example halides such as chloride or bromide and methosulfates. Examples of compounds of formula (Tkat1) are lauryltrimethylammonium chloride, cetyltrimethylammonium chloride, cetyltrimethylammonium bromide, cetyltrimethylammonium methosulfate, dicetyldimethylammonium chloride, tricetyl-methylammonium chloride, stearyltrimethylammonium chloride, distearyldimethylammonium chloride, lauryldimethylbenzylammonium chloride, behenyltrimethylammonium chloride, behenyltrimethylammonium bromide, behenyltrimethylammonium methosulfate. Preferred cosmetic agents contain a monomeric quaternary ammonium compound from the group of trimethylalkylammonium halides.

Further quaternary ammonium compounds which are more preferred according to the disclosure are the cationic betaine esters of formula (Tkat1-2.1).

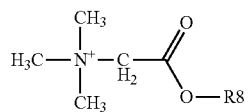
(Tkat1-2.1)

More preferred esterquats are those with the trade names Armocare VGH-70, and Dehyquart® F-75, Dehyquart® L80, Stepantex® VS 90 and Akypoquat® 131.

A further group are quaternary imidazoline compounds. The formula (Tkat2) illustrated below shows the structure of these compounds.

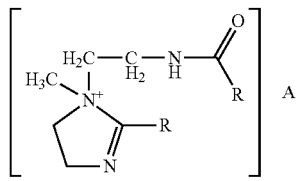
(Tkat2)

The residues R mutually independently in each case denote a saturated or unsaturated, linear or branched hydrocarbon residue with a chain length of 8 to 30 carbon atoms. The preferred compounds of the formula (Tkat2) in each case contain the identical hydrocarbon residue for R. The chain length of the residues R for example amounts to 12 to 21 carbon atoms. A denotes an anion as previously described. Examples which are particularly according to the disclosure are obtainable for example under INCI names Quaternium-27, Quaternium-72, Quaternium-83, Quaternium-87 and Quaternium-91. Quaternium-91 is most preferred according to the disclosure.

With regard to cosmetic action, advantageous cosmetic agents have proven to be those in which the proportion by weight of the monomeric quaternary ammonium compound in the total weight of the agent amounts to about 0.05 to about 3.0 wt. %, for example about 0.1 to about 2.0 wt. % and in particular about 0.2 to about 1.0 wt. %.

Suitable auxiliary substances and additives which may be mentioned are in particular additional conditioning substances.

The agent may for example contain at least one protein hydrolysate and/or one of the derivatives thereof as a conditioning substance of another compound class. Protein hydrolysates are product mixtures which are obtained by acidically, basically or enzymatically catalyzed degradation of proteins. According to the disclosure, the term protein hydrolysates also covers total hydrolysates and individual amino acids and the derivatives thereof and mixtures of different amino acids. The molecular weight of the protein hydrolysates which may be used according to the disclosure is between 75, the molecular weight of glycine, and 200,000, the molecular weight for example amounting to 75 to 50,000 and particularly for example to 75 to 20,000 daltons.

The agent according to the disclosure may furthermore contain at least one vitamin, a provitamin, a vitamin precursor and/or one of the derivatives thereof as a conditioning substance. Preferred vitamins, provitamins and vitamin precursors according to the disclosure are those which are conventionally assigned to groups A, B, C, E, F and H.

Like the addition of glycerol and/or propylene glycol, the addition of panthenol increases the flexibility of the polymer film formed using the agent according to the disclosure.

The agents according to the disclosure may furthermore contain at least one plant extract, but also mono- or oligosaccharides and/or lipids as conditioning substance.

Oil bodies are furthermore suitable as a conditioning substance. Natural and synthetic cosmetic oil bodies include, for example, vegetable oils, liquid paraffin oils, isoparaffin oils and synthetic hydrocarbons and di-n-alkyl ethers having a total of between 12 and 36 C atoms, in particular 12 to 24 C atoms. Preferred cosmetic agents according to the disclosure contain at least one oil body, for example at least one oil body from the group of silicone oils. The group of silicone oils in particular includes dimethicones, which also include cyclomethicones, amino-functional silicones and dimethiconols. The dimethicones may be both linear and branched and cyclic or cyclic and branched. Suitable silicone oils or silicone gums are in particular dialkyl- and alkylarylsiloxanes, such as for example dimethylpolysiloxane and methylphenylpolysiloxane, and the alkoxylated, quaternized or also anionic derivatives thereof. Preference is given to cyclic and linear polydialkylsiloxanes, the alkoxylated and/or aminated derivatives thereof, dihydroxypolydimethylsiloxanes and polyphenylalkylsiloxanes.

Ester oils, i.e. esters of $C_6$-$C_{30}$ fatty acids with $C_2$-$C_{30}$ fatty alcohols, for example monoesters of fatty acids with alcohols having 2 to 24 C atoms such as for example isopropyl myristate (Rilanit® IPM), isononanoic acid $C_{16-18}$ alkyl esters (Cetiol® SN), 2-ethylhexyl palmitate (Cegesoft® 24), stearic acid 2-ethylhexyl ester (Cetiol® 868), cetyl oleate, glycerol tricaprylate, coco fatty alcohol caprate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are further preferred conditioning oil bodies.

Additional suitable conditioning substances are dicarboxylic acid esters, symmetrical, asymmetrical or cyclic esters of carbonic acid with fatty alcohols, trifatty acid esters of saturated and/or unsaturated linear and/or branched fatty acids with glycerol, or fatty acid partial glycerides, which should be understood to mean monoglycerides, diglycerides and the technical mixtures thereof.

With regard to cosmetic action, advantageous cosmetic agents have proven to be those in which the proportion by weight of the oil body in the total weight of the agent amounts to about 0.01 to about 5.0 wt. %, for example about 0.02 to about 4.0 wt. % and in particular about 0.05 to about 2.0 wt. %.

The following tables show the composition of some preferred cosmetic agents (details in wt. % relative to the total weight of the cosmetic agent unless otherwise stated).

|  | Formula 1 | Formula 2 | Formula 3 | Formula 4 | Formula 5 |
| --- | --- | --- | --- | --- | --- |
| Copolymer A | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 6 | Formula 7 | Formula 8 | Formula 9 | Formula 10 |
| --- | --- | --- | --- | --- | --- |
| Copolymer A[1)] | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 11 | Formula 12 | Formula 13 | Formula 14 | Formula 15 |
| --- | --- | --- | --- | --- | --- |
| Copolymer A | 0.05 to 10 | 0.1 to 7.0 | 0.2 to 5.0 | 0.4 | 1.2 |
| Copolymer B[2)] | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 16 | Formula 17 | Formula 18 | Formula 19 | Formula 20 |
| --- | --- | --- | --- | --- | --- |
| Copolymer A[1)] | 0.05 to 10 | 0.1 to 7.0 | 0.2 to 5.0 | 0.4 | 1.2 |
| Copolymer B[2)] | 0.05 to 10 | 0.1 to 7.0 | 0.2 to 5.0 | 0.8 | 0.8 |
| Water, misc. | ad 100 | ad 100 | ad 100 | ad 100 | ad 100 |

|  | Formula 21 | Formula 22 | Formula 23 | Formula 24 | Formula 25 |
| --- | --- | --- | --- | --- | --- |
| Copolymer A | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Alkanolamine[3)] | 80 to 100 | 90 to 100 | 95 to 100 | 98 | 98 |
| Water, misc. | ad 100 | ad 100 | ad 100 | ad 100 | ad 100 |

|  | Formula 26 | Formula 27 | Formula 28 | Formula 29 | Formula 30 |
| --- | --- | --- | --- | --- | --- |
| Copolymer A[1)] | 0.05 to 10 | 0.1 to 7.0 | 0.2 to 5.0 | 0.4 | 1.2 |
| Copolymer B | 0.05 to 10 | 0.1 to 7.0 | 0.2 to 5.0 | 0.8 | 0.8 |
| Alkanolamine[3)] | 80 to 100 | 90 to 100 | 95 to 100 | 98 | 98 |
| Water, misc. | ad 100 | ad 100 | ad 100 | ad 100 | ad 100 |

|  | Formula 31 | Formula 32 | Formula 33 | Formula 34 | Formula 35 |
| --- | --- | --- | --- | --- | --- |
| Copolymer A | 0.05 to 10 | 0.1 to 7.0 | 0.2 to 5.0 | 0.4 | 1.2 |
| Copolymer B[2)] | 0.05 to 10 | 0.1 to 7.0 | 0.2 to 5.0 | 0.8 | 0.8 |
| Alkanolamine[3)] | 80 to 100 | 90 to 100 | 95 to 100 | 98 | 98 |
| Water, misc. | ad 100 | ad 100 | ad 100 | ad 100 | ad 100 |

|  | Formula 36 | Formula 37 | Formula 38 | Formula 39 | Formula 40 |
| --- | --- | --- | --- | --- | --- |
| Copolymer A[1)] | 0.05 to 10 | 0.1 to 7.0 | 0.2 to 5.0 | 0.4 | 1.2 |
| Copolymer B[2)] | 0.05 to 10 | 0.1 to 7.0 | 0.2 to 5.0 | 0.8 | 0.8 |
| Alkanolamine[3)] | 80 to 100 | 90 to 100 | 95 to 100 | 98 | 98 |
| Water, misc. | ad 100 | ad 100 | ad 100 | ad 100 | ad 100 |

|  | Formula 41 | Formula 42 | Formula 43 | Formula 44 | Formula 45 |
| --- | --- | --- | --- | --- | --- |
| Copolymer A[1)] | 0.05 to 10 | 0.1 to 7.0 | 0.2 to 5.0 | 0.4 | 1.2 |
| Copolymer B[2)] | 0.05 to 10 | 0.1 to 7.0 | 0.2 to 5.0 | 0.8 | 0.8 |
| 2-Amino-2-methylpropanol[3)] | 80 to 100 | 90 to 100 | 95 to 100 | 98 | 98 |
| Water, misc. | ad 100 | ad 100 | ad 100 | ad 100 | ad 100 |

|  | Formula 46 | Formula 47 | Formula 48 | Formula 49 | Formula 50 |
| --- | --- | --- | --- | --- | --- |
| Copolymer A[1)] | 0.05 to 10 | 0.1 to 7.0 | 0.2 to 5.0 | 0.4 | 1.2 |
| Copolymer B[2)] | 0.05 to 10 | 0.1 to 7.0 | 0.2 to 5.0 | 0.8 | 0.8 |
| Alkyltrimethyl-ammonium chloride | 0.05 to 3.0 | 0.1 to 2.0 | 0.2 to 1.0 | 0.5 | 0.3 |
| Water, misc. | ad 100 | ad 100 | ad 100 | ad 100 | ad 100 |

-continued

|  | Formula 51 | Formula 52 | Formula 53 | Formula 54 | Formula 55 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| Oil bodies | 0.01 to 5.0 | 0.02 to 4.0 | 0.05 to 2.0 | 0.1 | 0.1 |
| Water, misc. | ad 100 | ad 100 | ad 100 | ad 100 | ad 100 |

|  | Formula 56 | Formula 57 | Formula 58 | Formula 59 | Formula 60 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| Water | 40 to 99 | 50 to 98 | 60 to 95 | 97 | 92 |
| Misc. | ad 100 | ad 100 | ad 100 | ad 100 | ad 100 |

|  | Formula 61 | Formula 62 | Formula 63 | Formula 64 | Formula 65 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| Alkyltrimethyl-ammonium chloride | 0.05 to 3.0 | 0.1 to 2.0 | 0.2 to 1.0 | 0.5 | 0.3 |
| Water | 40 to 99 | 50 to 98 | 60 to 95 | 97 | 92 |
| Misc. | ad 100 | ad 100 | ad 100 | ad 100 | ad 100 |

|  | Formula 66 | Formula 67 | Formula 68 | Formula 69 | Formula 70 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| Oil bodies | 0.01 to 5.0 | 0.02 to 4.0 | 0.05 to 2.0 | 0.1 | 0.1 |
| Water | 40 to 99 | 50 to 98 | 60 to 95 | 97 | 92 |
| Misc. | ad 100 | ad 100 | ad 100 | ad 100 | ad 100 |

|  | Formula 71 | Formula 72 | Formula 73 | Formula 74 | Formula 75 |
|---|---|---|---|---|---|
| Copolymer A[1] | 0.05 to 10 | 0.1 to 7.0 | 0.2 to 5.0 | 0.4 | 1.2 |
| Copolymer B[2] | 0.05 to 10 | 0.1 to 7.0 | 0.2 to 5.0 | 0.8 | 0.8 |
| 2-Amino-2-methylpropanol[3] | 80 to 100 | 90 to 100 | 95 to 100 | 98 | 98 |
| Oil bodies | 0.01 to 5.0 | 0.02 to 4.0 | 0.05 to 2.0 | 0.1 | 0.1 |
| Water | 40 to 99 | 50 to 98 | 60 to 95 | 97 | 92 |
| Misc. | ad 100 | ad 100 | ad 100 | ad 100 | ad 100 |

[1] Copolymer A, which is based in a proportion of at least 95 wt. % on allyl methacrylate and one or more monomers from the group acrylic acid, methacrylic acid and one or more monomers from the group acrylic acid esters and methacrylic acid esters.
[2] Graft Copolymer of hydroxyethylcellulose with diallyldimethylammonium chloride
[3] % of the quantity required for complete neutralization of Copolymer A The cosmetic agents according to the disclosure may be formulated in any forms conventional for cosmetic agents, for example in the form of solutions, which may for example be applied onto the hair as a hair lotion, in the form of creams, emulsions, waxes, gels or also surfactant-containing foaming solutions or other preparations which are suitable for use on the hair. In an alternative embodiment, these agents may however also assume gel or cream form, wherein transparent gels are more preferred.

The compositions according to the disclosure are in particular highly suitable for stabilizing gas bubbles in the agent. In this way, air or other gases or gas mixtures can be readily incorporated into the agents according to the disclosure in such a manner as to be stable in the long-term. This may optionally proceed during production of the agents, by exposing the agent to gas, for example air, before packaging and packaging a product containing visible gas bubbles. The agents according to the disclosure for example assume the form of a foam. A foam is here a preparation comprising gas filled bubbles surrounded by liquid (liquid foam) or solid (stiff foam) walls. The compositions listed in the following table are for example stiff foams. The density of preferred compositions amounts to about 0.3 to about 1.0 g/cm$^3$, for example about 0.4 to about 0.9 g/cm$^3$ and in particular about 0.5 to about 0.8 g/cm$^3$. Such foams may for example be produced by beating the preparation in a suitable mixer or by exposure to a suitable gas, for example air.

The following tables show the composition of some preferred cosmetic foams. In this table the left-hand column ("formula x") refers in each case to one of the exemplary cosmetic compositions listed in the tables disclosed further above. The further columns two to seven ("density") in each case indicate the density of the corresponding cosmetic composition.

In other words, a cosmetic preparation according to line 12, column 5 of the following table comprises a cosmetic agent according to formula 11 with a density of 0.44 g/cm$^3$.

|  | Density [g/cm$^3$] | | | | | |
|---|---|---|---|---|---|---|
| Formula 1 | 0.3 to 1.0 | 0.93 | 0.4 to 0.9 | 0.44 | 0.5 to 0.8 | 0.61 |
| Formula 2 | 0.3 to 1.0 | 0.93 | 0.4 to 0.9 | 0.44 | 0.5 to 0.8 | 0.61 |
| Formula 3 | 0.3 to 1.0 | 0.93 | 0.4 to 0.9 | 0.44 | 0.5 to 0.8 | 0.61 |
| Formula 4 | 0.3 to 1.0 | 0.93 | 0.4 to 0.9 | 0.44 | 0.5 to 0.8 | 0.61 |
| Formula 5 | 0.3 to 1.0 | 0.93 | 0.4 to 0.9 | 0.44 | 0.5 to 0.8 | 0.61 |
| Formula 6 | 0.3 to 1.0 | 0.93 | 0.4 to 0.9 | 0.44 | 0.5 to 0.8 | 0.61 |
| Formula 7 | 0.3 to 1.0 | 0.93 | 0.4 to 0.9 | 0.44 | 0.5 to 0.8 | 0.61 |
| Formula 8 | 0.3 to 1.0 | 0.93 | 0.4 to 0.9 | 0.44 | 0.5 to 0.8 | 0.61 |
| Formula 9 | 0.3 to 1.0 | 0.93 | 0.4 to 0.9 | 0.44 | 0.5 to 0.8 | 0.61 |
| Formula 10 | 0.3 to 1.0 | 0.93 | 0.4 to 0.9 | 0.44 | 0.5 to 0.8 | 0.61 |
| Formula 11 | 0.3 to 1.0 | 0.93 | 0.4 to 0.9 | 0.44 | 0.5 to 0.8 | 0.61 |
| Formula 12 | 0.3 to 1.0 | 0.93 | 0.4 to 0.9 | 0.44 | 0.5 to 0.8 | 0.61 |
| Formula 13 | 0.3 to 1.0 | 0.93 | 0.4 to 0.9 | 0.44 | 0.5 to 0.8 | 0.61 |
| Formula 14 | 0.3 to 1.0 | 0.93 | 0.4 to 0.9 | 0.44 | 0.5 to 0.8 | 0.61 |
| Formula 15 | 0.3 to 1.0 | 0.93 | 0.4 to 0.9 | 0.44 | 0.5 to 0.8 | 0.61 |

-continued

|  | Density [g/cm³] | | | | | |
|---|---|---|---|---|---|---|
| Formula 16 | 0.3 to 1.0 | 0.93 | 0.4 to 0.9 | 0.44 | 0.5 to 0.8 | 0.61 |
| Formula 17 | 0.3 to 1.0 | 0.93 | 0.4 to 0.9 | 0.44 | 0.5 to 0.8 | 0.61 |
| Formula 18 | 0.3 to 1.0 | 0.93 | 0.4 to 0.9 | 0.44 | 0.5 to 0.8 | 0.61 |
| Formula 19 | 0.3 to 1.0 | 0.93 | 0.4 to 0.9 | 0.44 | 0.5 to 0.8 | 0.61 |
| Formula 20 | 0.3 to 1.0 | 0.93 | 0.4 to 0.9 | 0.44 | 0.5 to 0.8 | 0.61 |
| Formula 21 | 0.3 to 1.0 | 0.93 | 0.4 to 0.9 | 0.44 | 0.5 to 0.8 | 0.61 |
| Formula 22 | 0.3 to 1.0 | 0.93 | 0.4 to 0.9 | 0.44 | 0.5 to 0.8 | 0.61 |
| Formula 23 | 0.3 to 1.0 | 0.93 | 0.4 to 0.9 | 0.44 | 0.5 to 0.8 | 0.61 |
| Formula 24 | 0.3 to 1.0 | 0.93 | 0.4 to 0.9 | 0.44 | 0.5 to 0.8 | 0.61 |
| Formula 25 | 0.3 to 1.0 | 0.93 | 0.4 to 0.9 | 0.44 | 0.5 to 0.8 | 0.61 |
| Formula 26 | 0.3 to 1.0 | 0.93 | 0.4 to 0.9 | 0.44 | 0.5 to 0.8 | 0.61 |
| Formula 27 | 0.3 to 1.0 | 0.93 | 0.4 to 0.9 | 0.44 | 0.5 to 0.8 | 0.61 |
| Formula 28 | 0.3 to 1.0 | 0.93 | 0.4 to 0.9 | 0.44 | 0.5 to 0.8 | 0.61 |
| Formula 29 | 0.3 to 1.0 | 0.93 | 0.4 to 0.9 | 0.44 | 0.5 to 0.8 | 0.61 |
| Formula 30 | 0.3 to 1.0 | 0.93 | 0.4 to 0.9 | 0.44 | 0.5 to 0.8 | 0.61 |
| Formula 31 | 0.3 to 1.0 | 0.93 | 0.4 to 0.9 | 0.44 | 0.5 to 0.8 | 0.61 |
| Formula 32 | 0.3 to 1.0 | 0.93 | 0.4 to 0.9 | 0.44 | 0.5 to 0.8 | 0.61 |
| Formula 33 | 0.3 to 1.0 | 0.93 | 0.4 to 0.9 | 0.44 | 0.5 to 0.8 | 0.61 |
| Formula 34 | 0.3 to 1.0 | 0.93 | 0.4 to 0.9 | 0.44 | 0.5 to 0.8 | 0.61 |
| Formula 35 | 0.3 to 1.0 | 0.93 | 0.4 to 0.9 | 0.44 | 0.5 to 0.8 | 0.61 |
| Formula 36 | 0.3 to 1.0 | 0.93 | 0.4 to 0.9 | 0.44 | 0.5 to 0.8 | 0.61 |
| Formula 37 | 0.3 to 1.0 | 0.93 | 0.4 to 0.9 | 0.44 | 0.5 to 0.8 | 0.61 |
| Formula 38 | 0.3 to 1.0 | 0.93 | 0.4 to 0.9 | 0.44 | 0.5 to 0.8 | 0.61 |
| Formula 39 | 0.3 to 1.0 | 0.93 | 0.4 to 0.9 | 0.44 | 0.5 to 0.8 | 0.61 |
| Formula 40 | 0.3 to 1.0 | 0.93 | 0.4 to 0.9 | 0.44 | 0.5 to 0.8 | 0.61 |
| Formula 41 | 0.3 to 1.0 | 0.93 | 0.4 to 0.9 | 0.44 | 0.5 to 0.8 | 0.61 |
| Formula 42 | 0.3 to 1.0 | 0.93 | 0.4 to 0.9 | 0.44 | 0.5 to 0.8 | 0.61 |
| Formula 43 | 0.3 to 1.0 | 0.93 | 0.4 to 0.9 | 0.44 | 0.5 to 0.8 | 0.61 |
| Formula 44 | 0.3 to 1.0 | 0.93 | 0.4 to 0.9 | 0.44 | 0.5 to 0.8 | 0.61 |
| Formula 45 | 0.3 to 1.0 | 0.93 | 0.4 to 0.9 | 0.44 | 0.5 to 0.8 | 0.61 |
| Formula 46 | 0.3 to 1.0 | 0.93 | 0.4 to 0.9 | 0.44 | 0.5 to 0.8 | 0.61 |
| Formula 47 | 0.3 to 1.0 | 0.93 | 0.4 to 0.9 | 0.44 | 0.5 to 0.8 | 0.61 |
| Formula 48 | 0.3 to 1.0 | 0.93 | 0.4 to 0.9 | 0.44 | 0.5 to 0.8 | 0.61 |
| Formula 49 | 0.3 to 1.0 | 0.93 | 0.4 to 0.9 | 0.44 | 0.5 to 0.8 | 0.61 |
| Formula 50 | 0.3 to 1.0 | 0.93 | 0.4 to 0.9 | 0.44 | 0.5 to 0.8 | 0.61 |
| Formula 51 | 0.3 to 1.0 | 0.93 | 0.4 to 0.9 | 0.44 | 0.5 to 0.8 | 0.61 |
| Formula 52 | 0.3 to 1.0 | 0.93 | 0.4 to 0.9 | 0.44 | 0.5 to 0.8 | 0.61 |
| Formula 53 | 0.3 to 1.0 | 0.93 | 0.4 to 0.9 | 0.44 | 0.5 to 0.8 | 0.61 |
| Formula 54 | 0.3 to 1.0 | 0.93 | 0.4 to 0.9 | 0.44 | 0.5 to 0.8 | 0.61 |
| Formula 55 | 0.3 to 1.0 | 0.93 | 0.4 to 0.9 | 0.44 | 0.5 to 0.8 | 0.61 |
| Formula 56 | 0.3 to 1.0 | 0.93 | 0.4 to 0.9 | 0.44 | 0.5 to 0.8 | 0.61 |
| Formula 57 | 0.3 to 1.0 | 0.93 | 0.4 to 0.9 | 0.44 | 0.5 to 0.8 | 0.61 |
| Formula 58 | 0.3 to 1.0 | 0.93 | 0.4 to 0.9 | 0.44 | 0.5 to 0.8 | 0.61 |
| Formula 59 | 0.3 to 1.0 | 0.93 | 0.4 to 0.9 | 0.44 | 0.5 to 0.8 | 0.61 |
| Formula 60 | 0.3 to 1.0 | 0.93 | 0.4 to 0.9 | 0.44 | 0.5 to 0.8 | 0.61 |
| Formula 61 | 0.3 to 1.0 | 0.93 | 0.4 to 0.9 | 0.44 | 0.5 to 0.8 | 0.61 |
| Formula 62 | 0.3 to 1.0 | 0.93 | 0.4 to 0.9 | 0.44 | 0.5 to 0.8 | 0.61 |
| Formula 63 | 0.3 to 1.0 | 0.93 | 0.4 to 0.9 | 0.44 | 0.5 to 0.8 | 0.61 |
| Formula 64 | 0.3 to 1.0 | 0.93 | 0.4 to 0.9 | 0.44 | 0.5 to 0.8 | 0.61 |
| Formula 65 | 0.3 to 1.0 | 0.93 | 0.4 to 0.9 | 0.44 | 0.5 to 0.8 | 0.61 |
| Formula 66 | 0.3 to 1.0 | 0.93 | 0.4 to 0.9 | 0.44 | 0.5 to 0.8 | 0.61 |
| Formula 67 | 0.3 to 1.0 | 0.93 | 0.4 to 0.9 | 0.44 | 0.5 to 0.8 | 0.61 |
| Formula 68 | 0.3 to 1.0 | 0.93 | 0.4 to 0.9 | 0.44 | 0.5 to 0.8 | 0.61 |
| Formula 69 | 0.3 to 1.0 | 0.93 | 0.4 to 0.9 | 0.44 | 0.5 to 0.8 | 0.61 |
| Formula 70 | 0.3 to 1.0 | 0.93 | 0.4 to 0.9 | 0.44 | 0.5 to 0.8 | 0.61 |
| Formula 71 | 0.3 to 1.0 | 0.93 | 0.4 to 0.9 | 0.44 | 0.5 to 0.8 | 0.61 |
| Formula 72 | 0.3 to 1.0 | 0.93 | 0.4 to 0.9 | 0.44 | 0.5 to 0.8 | 0.61 |
| Formula 73 | 0.3 to 1.0 | 0.93 | 0.4 to 0.9 | 0.44 | 0.5 to 0.8 | 0.61 |
| Formula 74 | 0.3 to 1.0 | 0.93 | 0.4 to 0.9 | 0.44 | 0.5 to 0.8 | 0.61 |
| Formula 75 | 0.3 to 1.0 | 0.93 | 0.4 to 0.9 | 0.44 | 0.5 to 0.8 | 0.61 |

In an alternative embodiment, the cosmetic agents according to the disclosure may be packaged as pump or aerosol sprays. In addition to further active and auxiliary substances, preferred aerosol sprays contain a propellant. Propellants (propellant gases) suitable according to the disclosure are propane, n-butane, iso-butane, dimethyl ether (DME), nitrogen, air, nitrous oxide, 1,1-difluoroethane, specifically both individually and in combination. Hydrophilic propellant gases, such as for example carbon dioxide, may also advantageously be used for the purposes of the present disclosure if a small proportion of hydrophilic gases is selected and a lipophilic propellant gas (for example propane/butane) is present in excess. Dimethyl ether, propane, n-butane, iso-butane and mixtures of these propellant gases are more preferred. The use of propane/butane mixtures or isobutane is particularly preferred. Cosmetic agents which, relative to the total weight thereof, contain the propellant in a quantity of 2.0-20 wt. %, for example about 4.0-15 wt. % and such as about 5.0-10 wt. %, are preferred according to the disclosure.

The following tables show the composition of some preferred propellant-containing cosmetic agents. In this table the left-hand column ("formula x") refers in each case to one of the exemplary cosmetic compositions listed in the tables disclosed further above. The further columns two to seven ("propellant") in each case indicate the quantity of propellant added to the corresponding cosmetic composition. These indications in "wt. %" relate to the total weight of the cosmetic composition of the respective "formula x" without propellant.

In other words, a cosmetic preparation according to line 12, column 5 of the following table comprises an about 20:1 mixture of the propellant-free cosmetic agent according to formula 11 with a propane/butane mixture.

|  | Propellant [wt. %] | | | | | |
|---|---|---|---|---|---|---|
| Formula 1 | 2.0 to 10 | 5.0 | 2.0 to 10 P/B* | 5.0 P/B | 2.0 to 10 iB** | 5.0 iB |
| Formula 2 | 2.0 to 10 | 5.0 | 2.0 to 10 P/B* | 5.0 P/B | 2.0 to 10 iB** | 5.0 iB |
| Formula 3 | 2.0 to 10 | 5.0 | 2.0 to 10 P/B* | 5.0 P/B | 2.0 to 10 iB** | 5.0 iB |
| Formula 4 | 2.0 to 10 | 5.0 | 2.0 to 10 P/B* | 5.0 P/B | 2.0 to 10 iB** | 5.0 iB |
| Formula 5 | 2.0 to 10 | 5.0 | 2.0 to 10 P/B* | 5.0 P/B | 2.0 to 10 iB** | 5.0 iB |
| Formula 6 | 2.0 to 10 | 5.0 | 2.0 to 10 P/B* | 5.0 P/B | 2.0 to 10 iB** | 5.0 iB |
| Formula 7 | 2.0 to 10 | 5.0 | 2.0 to 10 P/B* | 5.0 P/B | 2.0 to 10 iB** | 5.0 iB |
| Formula 8 | 2.0 to 10 | 5.0 | 2.0 to 10 P/B* | 5.0 P/B | 2.0 to 10 iB** | 5.0 iB |
| Formula 9 | 2.0 to 10 | 5.0 | 2.0 to 10 P/B* | 5.0 P/B | 2.0 to 10 iB** | 5.0 iB |
| Formula 10 | 2.0 to 10 | 5.0 | 2.0 to 10 P/B* | 5.0 P/B | 2.0 to 10 iB** | 5.0 iB |
| Formula 11 | 2.0 to 10 | 5.0 | 2.0 to 10 P/B* | 5.0 P/B | 2.0 to 10 iB** | 5.0 iB |
| Formula 12 | 2.0 to 10 | 5.0 | 2.0 to 10 P/B* | 5.0 P/B | 2.0 to 10 iB** | 5.0 iB |
| Formula 13 | 2.0 to 10 | 5.0 | 2.0 to 10 P/B* | 5.0 P/B | 2.0 to 10 iB** | 5.0 iB |
| Formula 14 | 2.0 to 10 | 5.0 | 2.0 to 10 P/B* | 5.0 P/B | 2.0 to 10 iB** | 5.0 iB |
| Formula 15 | 2.0 to 10 | 5.0 | 2.0 to 10 P/B* | 5.0 P/B | 2.0 to 10 iB** | 5.0 iB |
| Formula 16 | 2.0 to 10 | 5.0 | 2.0 to 10 P/B* | 5.0 P/B | 2.0 to 10 iB** | 5.0 iB |
| Formula 17 | 2.0 to 10 | 5.0 | 2.0 to 10 P/B* | 5.0 P/B | 2.0 to 10 iB** | 5.0 iB |
| Formula 18 | 2.0 to 10 | 5.0 | 2.0 to 10 P/B* | 5.0 P/B | 2.0 to 10 iB** | 5.0 iB |
| Formula 19 | 2.0 to 10 | 5.0 | 2.0 to 10 P/B* | 5.0 P/B | 2.0 to 10 iB** | 5.0 iB |
| Formula 20 | 2.0 to 10 | 5.0 | 2.0 to 10 P/B* | 5.0 P/B | 2.0 to 10 iB** | 5.0 iB |

-continued

| | Propellant [wt. %] | | | | | |
|---|---|---|---|---|---|---|
| Formula 21 | 2.0 to 10 | 5.0 | 2.0 to 10 P/B* | 5.0 P/B | 2.0 to 10 iB** | 5.0 iB |
| Formula 22 | 2.0 to 10 | 5.0 | 2.0 to 10 P/B* | 5.0 P/B | 2.0 to 10 iB** | 5.0 iB |
| Formula 23 | 2.0 to 10 | 5.0 | 2.0 to 10 P/B* | 5.0 P/B | 2.0 to 10 iB** | 5.0 iB |
| Formula 24 | 2.0 to 10 | 5.0 | 2.0 to 10 P/B* | 5.0 P/B | 2.0 to 10 iB** | 5.0 iB |
| Formula 25 | 2.0 to 10 | 5.0 | 2.0 to 10 P/B* | 5.0 P/B | 2.0 to 10 iB** | 5.0 iB |
| Formula 26 | 2.0 to 10 | 5.0 | 2.0 to 10 P/B* | 5.0 P/B | 2.0 to 10 iB** | 5.0 iB |
| Formula 27 | 2.0 to 10 | 5.0 | 2.0 to 10 P/B* | 5.0 P/B | 2.0 to 10 iB** | 5.0 iB |
| Formula 28 | 2.0 to 10 | 5.0 | 2.0 to 10 P/B* | 5.0 P/B | 2.0 to 10 iB** | 5.0 iB |
| Formula 29 | 2.0 to 10 | 5.0 | 2.0 to 10 P/B* | 5.0 P/B | 2.0 to 10 iB** | 5.0 iB |
| Formula 30 | 2.0 to 10 | 5.0 | 2.0 to 10 P/B* | 5.0 P/B | 2.0 to 10 iB** | 5.0 iB |
| Formula 31 | 2.0 to 10 | 5.0 | 2.0 to 10 P/B* | 5.0 P/B | 2.0 to 10 iB** | 5.0 iB |
| Formula 32 | 2.0 to 10 | 5.0 | 2.0 to 10 P/B* | 5.0 P/B | 2.0 to 10 iB** | 5.0 iB |
| Formula 33 | 2.0 to 10 | 5.0 | 2.0 to 10 P/B* | 5.0 P/B | 2.0 to 10 iB** | 5.0 iB |
| Formula 34 | 2.0 to 10 | 5.0 | 2.0 to 10 P/B* | 5.0 P/B | 2.0 to 10 iB** | 5.0 iB |
| Formula 35 | 2.0 to 10 | 5.0 | 2.0 to 10 P/B* | 5.0 P/B | 2.0 to 10 iB** | 5.0 iB |
| Formula 36 | 2.0 to 10 | 5.0 | 2.0 to 10 P/B* | 5.0 P/B | 2.0 to 10 iB** | 5.0 iB |
| Formula 37 | 2.0 to 10 | 5.0 | 2.0 to 10 P/B* | 5.0 P/B | 2.0 to 10 iB** | 5.0 iB |
| Formula 38 | 2.0 to 10 | 5.0 | 2.0 to 10 P/B* | 5.0 P/B | 2.0 to 10 iB** | 5.0 iB |
| Formula 39 | 2.0 to 10 | 5.0 | 2.0 to 10 P/B* | 5.0 P/B | 2.0 to 10 iB** | 5.0 iB |
| Formula 40 | 2.0 to 10 | 5.0 | 2.0 to 10 P/B* | 5.0 P/B | 2.0 to 10 iB** | 5.0 iB |
| Formula 41 | 2.0 to 10 | 5.0 | 2.0 to 10 P/B* | 5.0 P/B | 2.0 to 10 iB** | 5.0 iB |
| Formula 42 | 2.0 to 10 | 5.0 | 2.0 to 10 P/B* | 5.0 P/B | 2.0 to 10 iB** | 5.0 iB |
| Formula 43 | 2.0 to 10 | 5.0 | 2.0 to 10 P/B* | 5.0 P/B | 2.0 to 10 iB** | 5.0 iB |
| Formula 44 | 2.0 to 10 | 5.0 | 2.0 to 10 P/B* | 5.0 P/B | 2.0 to 10 iB** | 5.0 iB |
| Formula 45 | 2.0 to 10 | 5.0 | 2.0 to 10 P/B* | 5.0 P/B | 2.0 to 10 iB** | 5.0 iB |
| Formula 46 | 2.0 to 10 | 5.0 | 2.0 to 10 P/B* | 5.0 P/B | 2.0 to 10 iB** | 5.0 iB |
| Formula 47 | 2.0 to 10 | 5.0 | 2.0 to 10 P/B* | 5.0 P/B | 2.0 to 10 iB** | 5.0 iB |
| Formula 48 | 2.0 to 10 | 5.0 | 2.0 to 10 P/B* | 5.0 P/B | 2.0 to 10 iB** | 5.0 iB |
| Formula 49 | 2.0 to 10 | 5.0 | 2.0 to 10 P/B* | 5.0 P/B | 2.0 to 10 iB** | 5.0 iB |
| Formula 50 | 2.0 to 10 | 5.0 | 2.0 to 10 P/B* | 5.0 P/B | 2.0 to 10 iB** | 5.0 iB |
| Formula 51 | 2.0 to 10 | 5.0 | 2.0 to 10 P/B* | 5.0 P/B | 2.0 to 10 iB** | 5.0 iB |
| Formula 52 | 2.0 to 10 | 5.0 | 2.0 to 10 P/B* | 5.0 P/B | 2.0 to 10 iB** | 5.0 iB |
| Formula 53 | 2.0 to 10 | 5.0 | 2.0 to 10 P/B* | 5.0 P/B | 2.0 to 10 iB** | 5.0 iB |
| Formula 54 | 2.0 to 10 | 5.0 | 2.0 to 10 P/B* | 5.0 P/B | 2.0 to 10 iB** | 5.0 iB |
| Formula 55 | 2.0 to 10 | 5.0 | 2.0 to 10 P/B* | 5.0 P/B | 2.0 to 10 iB** | 5.0 iB |
| Formula 56 | 2.0 to 10 | 5.0 | 2.0 to 10 P/B* | 5.0 P/B | 2.0 to 10 iB** | 5.0 iB |
| Formula 57 | 2.0 to 10 | 5.0 | 2.0 to 10 P/B* | 5.0 P/B | 2.0 to 10 iB** | 5.0 iB |
| Formula 58 | 2.0 to 10 | 5.0 | 2.0 to 10 P/B* | 5.0 P/B | 2.0 to 10 iB** | 5.0 iB |
| Formula 59 | 2.0 to 10 | 5.0 | 2.0 to 10 P/B* | 5.0 P/B | 2.0 to 10 iB** | 5.0 iB |
| Formula 60 | 2.0 to 10 | 5.0 | 2.0 to 10 P/B* | 5.0 P/B | 2.0 to 10 iB** | 5.0 iB |
| Formula 61 | 2.0 to 10 | 5.0 | 2.0 to 10 P/B* | 5.0 P/B | 2.0 to 10 iB** | 5.0 iB |
| Formula 62 | 2.0 to 10 | 5.0 | 2.0 to 10 P/B* | 5.0 P/B | 2.0 to 10 iB** | 5.0 iB |
| Formula 63 | 2.0 to 10 | 5.0 | 2.0 to 10 P/B* | 5.0 P/B | 2.0 to 10 iB** | 5.0 iB |
| Formula 64 | 2.0 to 10 | 5.0 | 2.0 to 10 P/B* | 5.0 P/B | 2.0 to 10 iB** | 5.0 iB |
| Formula 65 | 2.0 to 10 | 5.0 | 2.0 to 10 P/B* | 5.0 P/B | 2.0 to 10 iB** | 5.0 iB |
| Formula 66 | 2.0 to 10 | 5.0 | 2.0 to 10 P/B* | 5.0 P/B | 2.0 to 10 iB** | 5.0 iB |
| Formula 67 | 2.0 to 10 | 5.0 | 2.0 to 10 P/B* | 5.0 P/B | 2.0 to 10 iB** | 5.0 iB |
| Formula 68 | 2.0 to 10 | 5.0 | 2.0 to 10 P/B* | 5.0 P/B | 2.0 to 10 iB** | 5.0 iB |
| Formula 69 | 2.0 to 10 | 5.0 | 2.0 to 10 P/B* | 5.0 P/B | 2.0 to 10 iB** | 5.0 iB |
| Formula 70 | 2.0 to 10 | 5.0 | 2.0 to 10 P/B* | 5.0 P/B | 2.0 to 10 iB** | 5.0 iB |
| Formula 71 | 2.0 to 10 | 5.0 | 2.0 to 10 P/B* | 5.0 P/B | 2.0 to 10 iB** | 5.0 iB |
| Formula 72 | 2.0 to 10 | 5.0 | 2.0 to 10 P/B* | 5.0 P/B | 2.0 to 10 iB** | 5.0 iB |
| Formula 73 | 2.0 to 10 | 5.0 | 2.0 to 10 P/B* | 5.0 P/B | 2.0 to 10 iB** | 5.0 iB |
| Formula 74 | 2.0 to 10 | 5.0 | 2.0 to 10 P/B* | 5.0 P/B | 2.0 to 10 iB** | 5.0 iB |
| Formula 75 | 2.0 to 10 | 5.0 | 2.0 to 10 P/B* | 5.0 P/B | 2.0 to 10 iB** | 5.0 iB |

*"P/B" corresponds to a propane/butane mixture
**"iB" corresponds to isobutane

As explained above, the agents according to the disclosure have advantageous hair-fixing properties. The present application therefore also provides a method for temporarily deforming keratinic fibers, in which a composition according to the disclosure is applied onto the keratinic fibers. The present application also provides use of a cosmetic agent according to the disclosure for temporarily deforming keratinic fibers. As explained above, the agents according to the disclosure are distinguished in particular by improved hold in the case of temporary deformation of keratinic fibers. The present application therefore additionally provides the use of a cosmetic agent according to the disclosure to improve hold in the case of temporary deformation of keratinic fibers.

EXAMPLES

The humidity resistance (High Humidity Curl Retention; HHCR) of the temporary hair deformation achieved using the following three hair cosmetic agents was determined

| | Disclosure 1 | Comparison 1 | Comparison 2 |
|---|---|---|---|
| Fixate G-100[1] | 4.80 | 5.77 | — |
| Celquat L-200[2] | 0.75 | — | 1.6 |
| Sodium benzoate | 0.3 | 0.3 | 0.3 |
| D-Panthenol (75%) | 0.2 | 0.2 | 0.2 |
| Dow Corning 939[3] | 0.2 | 0.2 | 0.2 |
| Dehyquart A CA[4] | 1.0 | 1.0 | 1.0 |
| Castor Oil, hydrogenated, 40 EO | 0.2 | 0.2 | 0.2 |

-continued

|  | Disclosure 1 | Comparison 1 | Comparison 2 |
|---|---|---|---|
| Perfume | 0.1 | 0.1 | 0.1 |
| Water, misc. | ad 100 | ad 100 | ad 100 |

[1]Copolymer with the INCI name AMP-Acrylates/Allyl Methacrylate Copolymer (26% in water)
[2]Modified hydroxyalkylcellulose (INCI: Polyquaternium-4, 94%)
[3]Silicone preparation (INCI: Amodimethicone, Trideceth-12, Cetrimonium Chloride)
[4]Trimethylhexadecylammonium chloride To determine High Humidity Curl Retention, standardized strands of hair from Kerling (item no. 827560) of the "European Natural" hair type, color 6/0, of a length ($L_{max}$) of 220 mm and a weight of 0.6 g were used. The strands were washed with a 12.5 wt. % sodium laureth sulfate solution by way of preparation. The strands of hair were dried overnight in a drying oven at 318 K.

0.18 g of the compositions were applied onto a strand of hair and rubbed in. The strand was then wound onto a curler (Fripac-medis, diameter 7 mm, item no. D-1203) and dried overnight at room temperature.

The curlers were carefully removed and the strands hung up. The length of the curls were in each case measured ($L_0$) and the strands placed in a conditioning cabinet. They were stored there at 294 K and a relative atmospheric humidity of 85% over a period of 6 h, after which the length of the curls was remeasured ($L_t$).

Five test strands per composition were correspondingly treated and measured.

High Humidity Curl Retention (HHCR) was calculated according to the following formula and the arithmetic mean of the HHCR values for the 5 test strands was determined for each composition:

$$HHCR = \frac{L_{max} - L_t}{L_{max} - L_0}$$

|  | Disclosure 1 | Comparison 1 | Comparison 2 |
|---|---|---|---|
| HHCR | 77% | 53% | 71% |

The measurement data reveal the synergistic action of the polymer combination according to the disclosure in composition Disclosure 1.

The invention claimed is:

1. A cosmetic agent for the temporary deformation of keratin fibers, containing in a cosmetically acceptable carrier
    a) 0.05 wt % to 10 wt % of at least one copolymer A of allyl methacrylate with one or more monomers selected from acrylic acid, methacrylic acid, acrylic acid esters and methacrylic acid esters
    b) at least one polymeric quaternary ammonium compound from the group of quaternized celluloses.

2. The cosmetic agent according to claim 1, containing in a cosmetically acceptable carrier at least one copolymer A of allyl methacrylate with
    one or more monomers a1) selected from acrylic acid and methacrylic acid; and
    one or more monomers a2) selected from acrylic acid esters and methacrylic acid esters.

3. The cosmetic agent according to claim 1, wherein copolymer B is selected from the group of graft copolymers of hydroxyethylcellulose with diallyldimethylammonium chloride.

4. The cosmetic agent according to claim 1, wherein the proportion by weight of copolymer B in the total weight of the agent amounts to about 0.05 to about 10 wt. %.

5. The cosmetic agent according to claim 1, wherein the cosmetic agent furthermore contains at least one alkanolamine.

6. The cosmetic agent according to claim 1, wherein it furthermore contains at least one monomeric quaternary ammonium compound.

7. The cosmetic agent according to claim 1, wherein it furthermore contains at least one oil body.

8. A method comprising: using the cosmetic agent according to claim 1 for temporarily deforming keratinic fibers.

9. A method for temporarily deforming keratinic fibers comprising applying the composition according to claim 1 onto the keratinic fibers.

* * * * *